United States Patent [19]

Eck et al.

[11] Patent Number: 4,600,790
[45] Date of Patent: Jul. 15, 1986

[54] SILICON COMPOUNDS CONTAINING SIC-BONDED BIURET GROUPS AND A METHOD FOR PREPARING THE SAME

[75] Inventors: Herbert Eck; Hartmut Menzel, both of Munich; Reinhard Jira; Alfred Prasse, both of Burghausen, all of Fed. Rep. of Germany

[73] Assignee: Wacker-Chemie GmbH, Munich, Fed. Rep. of Germany

[21] Appl. No.: 704,238

[22] Filed: Feb. 22, 1985

[30] Foreign Application Priority Data

Mar. 22, 1984 [DE] Fed. Rep. of Germany ....... 3410582

[51] Int. Cl.$^4$ ............... C07F 7/08; C07F 7/10
[52] U.S. Cl. .................... 556/421; 556/414; 528/18; 106/287.11
[58] Field of Search ............... 556/414, 421

[56] References Cited

U.S. PATENT DOCUMENTS

| 3,576,033 | 4/1971 | Tesoro et al. ............ 556/421 |
| 3,895,043 | 7/1975 | Wagner et al. ............ 556/421 X |
| 3,903,052 | 9/1975 | Wagner et al. ............ 556/421 X |
| 4,046,794 | 9/1977 | Pepe et al. ............ 556/421 |

FOREIGN PATENT DOCUMENTS

| 1812562 | 6/1970 | Fed. Rep. of Germany ...... 556/421 |
| 2243628 | 3/1974 | Fed. Rep. of Germany ...... 556/421 |

*Primary Examiner*—Paul F. Shaver

[57] ABSTRACT

Organosilicon compounds containing SiC-bonded biuret groups are prepared by (I) adding a silane containing 1 or 2 silicon atoms per molecule and an SiC-bonded organic radical having at least one basic

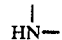

group and at least one SiOC-bonded aliphatic radical per molecule to a monoisocyanate or a diisocyanate at a temperature up to 125° C. and (II) maintaining the temperature at 110° C. to 125° C. for at least two minutes. In an alternate procedure the silane and mono- or diisocyanate may be heated to a temperature in the range of from 110° C. up to 200° C. for at least two minutes, after or while adding additional monoisocyanate or diisocyanate.

The resultant silicon compounds are used in the preparation of polyurethanes and as additives to lacquers.

14 Claims, No Drawings

SILICON COMPOUNDS CONTAINING SIC-BONDED BIURET GROUPS AND A METHOD FOR PREPARING THE SAME

The present invention relates to organosilicon compounds containing biuret groups, particularly to organosilicon compounds containing SiC-bonded biuret groups and more particularly to a method for preparing organosilicon compounds containing SiC-bonded biuret groups.

BACKGROUND OF THE INVENTION

Polymers containing alkoxy-substituted SiC-bonded biuret groups are described in German Offenlegungsschrift No. 22 43 628 and in Chemical Abstracts, Volume 81, 1974.

An object of the present invention is to prepare silicon compounds which contain SiC-bonded biuret groups. Another object of the present invention is to prepare silicon compounds which contain SiC-bonded biuret groups and SiOC-bonded aliphatic radicals. Still another object of the present invention is to prepare low molecular weight silicon polymers which contain SiC-bonded biuret groups and SiOC-bonded aliphatic radicals. A further object of the present invention is to provide a method for preparing monomeric or low molecular weight silicon polymers which contain SiC-bonded biuret groups and SiOC-bonded aliphatic radicals. A still further object of the present invention is to provide a method for preparing monomeric or low molecular weight silicon polymers having SiC-bonded biuret groups and SiOC-bonded aliphatic radicals in the absence of solvents.

SUMMARY OF THE INVENTION

The foregoing objects and others which will become apparent from the following description are accomplished in accordance with this invention, generally speaking, by providing silicon compounds containing SiC-bonded biuret groups and SiOC-bonded aliphatic radicals which are obtained from (I) the addition of a silane which contains 1 or 2 silicon atoms per molecule and an SiC-bonded radical having at least one basic

group and at least one SiOC-bonded aliphatic radical per molecule to an isocyanate selected from a monoisocyanate and/or a diisocyanate in an amount of at least 1 gram-equivalent of —NCO group per gram-equivalent of

group present in the silane at a temperature up to 125° C. and thereafter (II) the product obtained from Stage (I) is maintained at a temperature of from 110° C. to 125° C. for at least 2 minutes.

In another embodiment, when the amount of monoisocyanate employed from Stage (I) is less than 2 gram-equivalents of NCO groups or the amount of diisocyanate employed is less than 3 gram-equivalents of —NCO groups per gram equivalent of

group present in the silane, then the product of Stage (I) is heated in Stage (II) to a temperature of from 110° C. to 200° C. for at least two minutes after or during the addition of additional monoisocyanate or diisocyanate.

The silicon compounds of this invention containing SiC-bonded biuret groups and SiOC-bonded aliphatic radicals are prepared by:

(I) adding a silane which contains 1 or 2 silicon atoms per molecule and an SiC-bonded radical having at least one basic

group and at least one SiOC-bonded aliphatic radical per molecule to a monoisocyanate and/or a diisocyanate in an amount of at least 1 gram-equivalent of —NCO group per gram-equivalent of

group present in the silane at a temperature up to 125° C. and after the addition of the silane is complete, then (II) maintaining the product obtained from Stage (I) at a temperature of from 110° C. to 125° C. for at least 2 minutes.

In another embodiment of this invention, when the amount of monoisocyanate in Stage (I) is less than 2 gram-equivalents of —NCO groups or the amount of diisocyanate is less than 3 gram-equivalents of —NCO groups per gram-equivalent of

group present in the silane, then the product obtained from Stage (I) is heated in Stage (II) to a temperature in the range of from 110° to 200° C. for at least two minutes after, or during, the addition of additional monoisocyanate or diisocyanate.

DESCRIPTION OF THE INVENTION

The silanes used in the preparation of the silicon compounds of this invention preferably have the following formula

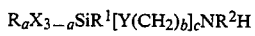

where R is the same or different hydrocarbon radicals; $R^1$ is the same or different divalent SiC-bonded organic radicals consisting of carbon, hydrogen and possibly basic nitrogen atoms; $R^2$ is hydrogen or the same or different monovalent hydrocarbon radicals or radicals of the formula

where R, and $R^1$ are the same as above; X is the same or different SiOC-bonded monovalent aliphatic radicals; Y is $-NR^2-$, $-O-$ or $-S-$ and a is 0, 1 or 2; b is 2, 3 or 4; and c is 0, 1, 2, 3 or 4.

Hydrocarbon radicals represented by R preferably contain from 1 to 4 carbon atoms per radical such as the methyl, ethyl, n-propyl, isopropyl, n-butyl, sec-butyl, vinyl, allyl and methallyl radicals.

When the radicals represented by X are SiOC-bonded hydrocarbon radicals, they preferably contain from 1 to 4 carbon atoms per radical such as the methoxy, ethoxy, n-propoxy, isopropoxy, n-butoxy, sec-butoxy, allyloxy, methallyloxy and isopropenyloxy radicals.

Moreover, the radicals represented by X can also be acyloxy radicals or a radical of the formula $-O(CH_2CH_2O)_nR^3$, in which $R^3$ is hydrogen or is the same as R and n is 1, 2, 3, or 4. The examples for hydrocarbon radicals represented by R are also equally applicable for the hydrocarbon radicals represented by $R^3$. The most important example of a radical represented by X other than SiOC-bonded hydrocarbon radicals is the methoxyethyleneoxy radical.

Examples of divalent SiC-bonded organic radicals consisting of carbon, hydrogen and possibly basic nitrogen atoms, and in particular have the formula $-[CH_{2-d}(CH_3)_d]_m-$, in which d is 0 or 1 and m is a whole number with a value of from 1 to 6,

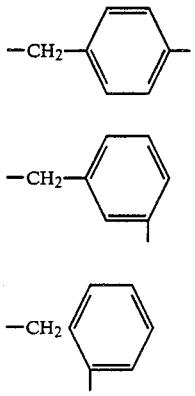

and the o-, m- and p-phenylene radicals.

The hydrocarbon radicals represented by $R^2$ can be aliphatic, cycloaliphatic or aromatic hydrocarbons, preferably having from 1 to 6 carbon atoms per radical. The hydrocarbon radicals represented by X having the SiOC-bonded hydrocarbon radicals, are also applicable for the hydrocarbon radicals represented by $R^2$, except for the isopropenyl radical. Other examples of hydrocarbon radicals represented by $R^2$ are the cyclohexyl and phenyl radicals. An example of the radical having the formula

is a radical of the formula

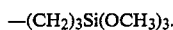

Specific examples of silanes which can be used in the preparation of the silicon compounds of this invention in Stage (I) have the formulas $(CH_3O)_3SiCH_2NH_2$ $CH_3(CH_3O)_2SiCH_2NH_2$ $(C_2H_5O)_3SiCH_2NH_2$ $(CH_3)_2CH_3OSiCH_2NH_2$ $(n-C_3H_7O)_3SiCH_2NH_2$ $CH_3(C_2H_5O)_2Si(CH_2)_3NH_2$ $(CH_3O)_3Si(CH_2)_3NH_2$ $(CH_3)_2C_2H_5OSi(CH_2)_3NH_2$ $(C_2H_5O)_3Si(CH_2)_3NH_2$ $(CH_3)_2(n-C_3H_7O)Si(CH_2)_3NH_2$ $(n-C_4H_9O)_3Si(CH_2)_3NH_2$ $CH_3(iso-C_3H_7O)_2Si(CH_2)_3NH_2$ $(C_2H_5O)_3SiCH_2C_6H_4NH_2$ $(CH_3O)_3Si(CH_2)_4NH_2$ $(CH_3O)_3Si(CH_2)_3NHCH_3$ $(CH_3O)_3Si(CH_2)_3NH-n-C_6H_{13}$ $(iso-C_3H_7O)_3Si(CH_2)_3NH-cyclo-C_6H_{11}$ $(CH_3O)(CH_3)_2Si(CH_2)_3NHC_6H_5$ $(C_2H_5O)_3SiCH_2CH(CH_3)NH_2$ $(C_2H_5O)_3SiCH(CH_3)CH_2NH_2$ $(CH_3OC_2H_4O)_3Si(CH_2)_3NH_2$ $(C_2H_5O)_3Si(CH_2)_3NH(CH_2)_2NH_2$ $(CH_3O)_3Si(CH_2)_3NH(CH_2)_2NH_2$ $(CH_3O)_3Si(CH_2)_3NH(CH_2)_2NH(CH_2)_3Si(OCH_3)_3.$ The monoisocyanates and/or diisocyanates used in the preparation of the silicon compounds of this invention can be the same or different. They may be aliphatic, cycloaliphatic, aromatic, alkaromatic or araliphatic monoisocyanates and/or diisocyanates. The aliphatic radicals present in the monoisocyanates and/or diisocyanates can be linear or branched and, like the cycloaliphatic, araliphatic or alkaromatic radicals present in the isocyanates, may be free of aliphatic carbon-carbon multiple bonds or may contain multiple bonds, in particular double bonds. Aside from being substituted by isocyanate groups, they may be substituted by groups which are inert with respect to the isocyanate groups, such as the epoxy or alkoxy groups or atoms, such as chlorine atoms. Preferably, the isocyanates used in the preparation of the silicon compounds of this invention contain at most 20 carbon atoms and more preferably not more than about 17 carbon atoms per molecule.

Specific examples of isocyanates which may be used in the preparation of the silicon compounds of this invention are hexamethylenediisocyanate, trimethylhexamethylenediisocyanate, diphenylmethane-4,4'- diisocyanate, allylisocyanate, phenylisocyanate, p-ethoxyphenylisocyanate, o-, p- and m-tolylisocyanate, naphthylenediisocyanates and toluylenediisocyanates. The preferred isocyanates are the aliphatic diisocyanates.

When the $R^1$ radical is free of basic nitrogen and when c is zero, the silicon compounds of this invention are prepared in Stages (I) and (II) in accordance with the following equations.

Stage (I):

$$R_aX_{3-a}SiR^1NR^2H + R^5(NCO)_{2-d} \rightarrow R_aX_{3-a}SiR^1NR^2CONHR^5(NCO)_{1-d}$$

Stage (II):

$$R_aX_{3-a}SiR^1NR^2CONHR^5(NCO)_d + R^5(NCO)_{2-d} \rightarrow R_aX_{3-a}SiR^1NR^2CONR^5(NCO)_dCONHR^5(NCO)_{1-d}$$

where R, $R^1$, X, a and d are the same as above, $R^2$ is a monovalent hydrocarbon radical or a radical of the formula $$R^1SiR_aX_{3-a}$$

and
$R^5$ is a monovalent or divalent, substituted or unsubstituted hydrocarbon radical.

In the above equation, when $R^2$ is hydrogen, then the silicon compound has the formula:

$$R_aX_{3-a}SiR^1NCOR^5(NCO)_{1-d}$$
$$|$$
$$CONHR^5(NCO)_{1-d}$$

The method of this invention can be carried out batchwise, semi-continuously or as a continuous process in a single apparatus without removing the product obtained in Stage (I) prior to initiating Stage (II).

In Stage (I) of the method of this invention, cooling may be required to prevent the temperature from exceeding 125° C. and more preferably 120° C.

Stage (II) of the method of this invention is preferably carried out at 120° C. to 170° C.

Residence times longer than one hour are not generally required in Stage (II).

When a monoisocyanate is employed, preferably 1 to 2 gram-equivalents of —NCO groups are present in the mixture used in Stage (II) per gram-equivalent of HN— group present in the silane used in Stage (I) and when a diisocyanate is employed, preferably 3 to 8 gram-equivalents of —NCO groups are preferably present in the mixture used in Stage (II) per gram-equivalent of $$|$$
$$HN-$$

group present in the silane used in Stage (I). Smaller amounts often result in undesirably low yields of biuret group-containing silicon compounds. Larger amounts do not produce any advantages.

Preferably, neither a solvent nor a catalyst are used in the method of this invention.

When the silicon compounds containing the SiC-bonded biuret groups of this invention contain at least 2 —NCO groups per molecule, they may be used as at least a part of the compounds containing at least 2 —NCO groups per molecule in the preparation of polyurethanes.

Polyurethanes are well known in the art and are prepared by reacting an organic compound having at least two active hydrogen atoms as determined by the Zerewitinoff method with a compound containing —NCO groups. Other reactants, such as chain extending agents and gas-generating materials may also be employed, depending on the particular polyurethane article desired. For example, in the formation of cellular materials, gas-generating materials, such as water, are generally incorporated in the composition.

Suitable examples of compounds containing —NCO groups other than the silicon compounds of this invention are alkylene diisocyanates, e.g., hexamethylene diisocyanate and decamethylene diisocyanate, and arylene diisocyanates, e.g., phenylene diisocyanates, toluene diisocyanates and mixtures thereof.

Compounds having two or more hydrogen atoms are determined by the Zerewitinoff method are polyalkylene polyols such as polyesters, polyethers, alkylene glycols, polymercaptans, polyamines and the like.

Compounds which have been employed as catalysts or activators in the formation of polyurethanes are amines such as N-ethylmorpholine and tetramethyl-1,4-butane diamine; tin compounds such as dibutyltin di-2-ethyl hexoate, dibutyltin dilaurate, stannous-2-ethylhexoate, stannous oleate; and metal soaps such as ferrous distearate, manganous linoleate, nickel stearate, cobalt stearate, manganese stearate, ferrous linoleate and cobalt naphthenate. Preferably the silicon compounds of this invention are used in an amount of from 0.1 to 0.6 mols, calculated as the silane used in their preparation, per mol of organic diisocyanate.

Also, the silicon compounds of this invention contain SiC-bonded biuret groups may be used as additives for lacquers. These additives improve the adhesion of the lacquer to substrates such as glass, metal or organopolysiloxane elastomers. Polyurethane, epoxide and alkyd resin lacquers are examples of lacquers in which these silicon compounds may be added.

Preferably, the biuret group-containing compounds are used in the lacquers in an amount of from 0.5 to 10 percent by weight based on the weight of the lacquer to be mixed with the biuret group-containing silicon compound.

The silicon compounds of this invention containing SiC-bonded biuret groups may be incorporated into polymers other than the polyurethanes described above when they contain —NCO groups or carbon-carbon double bonds. Since these silicon compounds contain SiOC-bonded aliphatic radicals, they may be incorporated into polymers which crosslink upon exposure to moisture in the air. These silicon compounds may be used in, for example, applications in which the biuret group-containing silicon compounds are a component of composites, sealant compositions including those based on organopolysiloxanes, metalpolyurethane laminates and insulating materials.

In the following examples, all parts and percentages are by weight unless otherwise specified.

EXAMPLES 1 TO 4

Preparation of the silicon compounds of the invention

Stage (I): A silane is added dropwise in the amount shown in Table I over a period of from 5 to 10 minutes to a flask containing the isocyanate shown in the table, which is equipped with a reflux condenser, addition funnel, stirrer and thermometer. The temperature of the contents of the flask increases to the temperature indicated in the table.

Stage (II): After the silane has been added, the contents of the flask are heated to the temperature and for the time indicated in the table and then rapidly cooled to room temperature.

TABLE 1

| | Stage I | | | | | Stage II | |
|---|---|---|---|---|---|---|---|
| Ex. | Silane | Moles | Isocyanate | Moles | Temp. rises to °C. | Temp. °C. | Time in minute(s) |
| 1 | $H_2N(CH_2)_3Si(OC_2H_5)_3$ | 1 | HMD | 2 | ca. 70 | 155 | 10 |
| 2 | " | 1 | " | 2 | ca. 70 | 160 | 10 |
| 3 | " | 1 | " | 2 | ca. 70 | 150 | 5 |
| 4 | " | 0.25 | " | 1.5 | ca. 70 | 140 | 10 |
| 5 | " | 0.25 | TMHMD | 1.5 | ca. 60 | 150 | 10 |
| 6 | " | 0.25 | DPMD | 1.5 | ca. 100 | 140 | 5 |
| 7 | " | 1 | AI | 6 | 60 | 125 | 5 (1.8 bar abs.) |
| 8 | " | 1 | PPI | 4 | 60 | 150 | 10 |
| 9 | $H_2N(CH_2)_2NH(CH_2)_3Si(OCH_3)_3$ | 0.25 | HMD | 1.5 | 70 | 150 | 10 |
| 10 | " | 0.25 | " | 1.5 | 75 | 230 | 1 |
| 11 | " | 0.25 | " | 1.75 | 75 | 160 | 10 |
| 12 | $p\text{-}H_2NC_6H_4Si(OC_2H_5)_3$ | 1 | " | 2 | 75 | 165 | 10 |
| 13 | $n\text{-}C_6H_{13}NH(CH_2)_3Si(OCH_3)_3$ | 1 | " | 2 | 65 | 180 | 60 |
| 14 | $CH_3NH(CH_2)_3Si(OC_2H_5)_3$ | 1 | " | 2 | 85 | 180 | 30 |

HMD = hexamethylenediisocyanate
TMHMD = trimethylhexamethylenediisocyanate
DPMD = diphenylmethane-4,4'-diisocyanate
AI = allylisocyanate
PI = phenylisocyanate

EXAMPLES 15 TO 18

Preparation of polyurethane

A high-molecular weight diol of the type and amount indicated in Table 2, and a silicon compound containing a biuret group, prepared in accordance with the example specified and in the amount specified in Table 2, is stirred at 80° C. with a diisocyanate of the type and quantity indicated in Table 2. The mixtures thus obtained are mixed with butanediol in the quantity indicated in Table 2 and then heated in polyethylene shells, initially at 80° C. for 2.5 hours and then at 120° C. for 2.5 hours (Example 15). In Examples 16, 17 and 18 the mixtures are initially heated at 80° C. for 1 hour and then at 120° C. for 4 hours. The properties of the resultant products are shown in Table 2.

COMPARISON EXAMPLE $V_1$

The procedure of Example 18 is repeated except that 0.5 mols of 1,4-butanediol are substituted for the 0.252 mols of 1,4-butanediol; 1.62 mols of hexamethylenediisocyanate are substituted for the 1.35 mols of hexamethylenediisocyanate and no biuret group-containing silicon compound is used. A partially liquid product is obtained.

COMPARISON EXAMPLE $V_2$

The procedure of Example 16 is repeated, except that 0.262 mols of 1,4-butanediol are substituted for the 0.295 mols of butanediol; 1.44 mols of hexamethylenediisocyanate are substituted for the 1.35 mols of hexamethylenediisocyanate and 0.25 mols of n-butylamine are used instead of the biuret group-containing silicon compound. After heating, the adhesion on glass and aluminum is 0 in each case.

EXAMPLE 19

One mol of the silicon compound containing the biuret group (calculated as the silane used in its preparation) is stirred at 80° C. together with 0.476 mols of hexamethylenediisocyanate into 1 mol of ethylene glycol-adipic acid polyester in which the terminal groups are essentially $HOCH_2$ groups and have a molecular weight of 2000 (Polyester D 2020, Bayer, Leverkusen). The resulting mixture is mixed with 0.2 mols of 1,4-butanediol and then heated in a polyethylene shell, initially at 80° C. for 1 hour and then at 150° C. for 1.5 hours.

A hard product is obtained having good tear resistance and a satisfactory tear propagation strength.

| Adhesion after heating to | $N/mm^2$ |
|---|---|
| Glass | 6.8 |
| Aluminum | 4.7 |

EXAMPLE 20

About 0.508 mols of hexamethylenediisocyanate and 0.66 g of diazabicyclooctane are stirred at 100° C. into 1 mol of ethylene glycol-adipic acid polyester in which the terminal groups are essentially $HOCH_2$ groups and have a molecular weight of 2000 (Polyester D 2020, Bayer, Leverkusen). The mixture, which is still about 100° C., is added to a mixture consisting of 0.66 g of dibutyltin dilaurate, 0.2 mols of 1,4-butanediol and 1.0 mol of the silicon compound containing the biuret group, (calculated as the silane used in its preparation in accordance with Example 2). Crosslinking of the mixture is observed after approximately 50 seconds.

After approximately 1.5 hours, a tack-free, hard product is obtained having a very good tear resistance and a satisfactory to good tear propagation strength.

| Adhesion after heating to | $N/mm^2$ |
|---|---|
| Glass | 3.4 |
| Aluminum | 3.15 |

TABLE 2

| Example | Moles | High Molecular Weight Diol | Molecular Weight of Diol | Moles* | Si Compound Containing Biuret Group Prepared In Example Number | Moles | Diisocyanate | Moles 1,4-butanediol |
|---|---|---|---|---|---|---|---|---|
| 15 | 0.99 | Polyester** | 2000 | 0.25 | 2 | 1.25 | HMGD | 0.252 |
| 16 | 1 | Polyester** | 2000 | 0.27 | 2 | 1.35 | HMGD | 0.295 |
| 17 | 1 | Polyester** | 2000 | 0.27 | 5 | 1.35 | TMHMD | 0.253 |
| 18 | 1 | PTHF | 1000 | 0.27 | 1 | 1.35 | HMGD | 0.252 |

| Example | Tear Resistance | Tear Propagation* Strength | Hardness | Adhesion after* Heating To Glass | Adhesion after* Heating To Aluminum | Running Upon Heating at 120° C. to 180° C. |
|---|---|---|---|---|---|---|
| 15 | Very Good | Very Good | Good | Sat. | Good | Barely |
| 16 | Very Good | Very Good | Good | Sat. | 0 | None |
| 17 | Very Good | Good | Good | Good | Good | Yes |
| 18 | Very Good | Very Good | Sat. | Sat. | Sat. | Barely |

Polyester**: Ethylene glycol-adipic acid polyester in which the terminal groups are essentially HOCH$_2$ (Polyester D 2020, Bayer, Leverkusen).
*Calculated as silane used for its preparation.
HMGD = Hexamethylene glycol diisocyanate.
TMHMD = Trimethylhexamethylenediisocyanate.
PTHF = Polytetrahydrofuran.
*Determined manually without a measuring instrument.
Sat. = Satisfactory.

COMPARISON EXAMPLE V$_3$

The procedure of Example 20 is repeated, except that 1.0 mol of 1,4-butanediol and 2.6 mols of hexamethylenediisocyanate are substituted for the 0.2 mols of 1,4-butanediol, 0.508 mols of hexamethylenediisocyanate and the silicon compound containing the biuret group. Crosslinking is observed after approximately 5 minutes.

The tear resistance is satisfactory to good, the tear propagation strength is low and the adhesion on glass and aluminum after heating is 0.

EXAMPLES 21 TO 23

Addition of silicon compounds containing SiC-bonded biuret groups to a lacquer (a) About 45 parts of a silicon compound containing biuret groups prepared in accordance with Example 2 are mixed with 7 parts of di-2-ethylhexyltin dilaurate, 45 parts of toluene and 3 parts of polydimethylsiloxane-polyoxyethylene block copolymer.

(b) About 6 parts of the mixture prepared in (a) above are mixed with 94 parts of the lacquer indicated in Table 3. The mixture containing lacquer and additive is applied to a tack-free skin which forms over the uncrosslinked portion of the organopolysiloxane-based composition indicated in Table 3, which can be stored in the absence of moisture and is crosslinked to an elastomer upon exposure to moisture. One hour after this coating is applied, another coating of the same type is applied to this lacquer layer, except that the additive has been omitted. The results are shown in Table 3.

COMPARISON EXAMPLES V$_4$, V$_5$ and V$_6$

The procedures of Examples 21 to 23 are repeated, except that 45 parts by weight of a silane of the formula $$H_2N(CH_2)_2NH(CH_2)_3Si(OC_2H_5)_3$$

are substituted for the 45 parts by weight of silicon compound containing the biuret group.

The results are shown in Table 3.

TABLE 3

| Example or Comparison Example | Type of Composition Crosslinkable to Elastomer | Lacquer | Coatability | Adhesion on elastomer+ |
|---|---|---|---|---|
| 21 | Crosslinks with the liberation of amine and oxime. | Two component polyurethane lacquer. | Coatable | Good |
| V$_4$ | Crosslinks with the liberation of amine and oxime. | Two component polyurethane lacquer. | Coatable | None |
| 22 | Crosslinks with the liberation of amine and oxime. | One component epoxide lacquer. | Coatable | Good |
| V$_5$ | Crosslinks with the liberation of amine and oxime. | One component epoxide lacquer. | Coatable, but with 5 percent uncovered sites on skin. | Moderate |
| 23 | Composition of the above type, but with chalk as filler. | Alkyd resin lacquer. | Coatable | Moderate |
| V$_6$ | Composition of the above type, but with chalk as filler. | Alkyl resin lacquer. | Coatable | Somewhat worse than moderate. |

+Good = Lacquer layer cannot be removed without damaging elastomer.
Moderate = Lacquer layer can be removed only in pieces up to 1 cm$^2$.
None = Lacquer layer can be easily removed in one piece or in a few pieces.

What is claimed is:

1. Silicon compounds containing SiC-bonded biuret groups and SiOC-bonded aliphatic radicals which are obtained by (I) the addition of a silane containing up to 2 silicon atoms per molecule and an SiC-bonded organic radical which has at least one basic

group and at least one SiOC-bonded aliphatic radical per molecule to an isocyanate selected from the group consisting of a monoisocyanate, a diisocyanate and mixtures thereof in an amount of at least 1 gram-equivalent of —NCO group per gram-equivalent of

group present in the silane at a temperature up to 125° C.; and thereafter (II) the product obtained in (I) is maintained for at least 2 minutes at a temperature of from 110° C. to 125° C.

2. The silicon compounds of claim 1, wherein a monoisocyanate is used in Stage (I) in an amount up to 2 gram-equivalents of —NCO groups per gram-equivalent of

group present in the silane and the product obtained from Stage (I) is heated to a temperature in the range of from 110° C. to 200° C. for at least two minutes in Stage (II) after or during the addition of additional isocyanate.

3. The silicon compounds of claim 1, wherein a diisocyanate is used in Stage (I) in an amount up to 3 gram-equivalents of —NCO groups per gram-equivalent of

group present in the silane and the product obtained from Stage (I) is heated to a temperature in the range of from 110° C. to 200° C. for at least two minutes in Stage (II) after or during the addition of additional isocyanate.

4. A method for preparing silicon compounds containing SiC-bonded biuret groups and SiOC-bonded aliphatic radicals which comprises adding (I) a silane containing up to 2 silicon atoms per molecule and an SiC-bonded organic radical which has at least one basic

group and at least one SiOC-bonded aliphatic radical per molecule to an isocyanate selected from the group consisting of a monoisocyanate, a diisocyanate and mixtures thereof in an amount of at least 1 gram-equivalent of —NCO group per gram-equivalent of

group present in the silane at a temperature up to 125° C.; and thereafter (II) maintaining the product obtained in (I) for at least 2 minutes at 110° C. to 125° C.

5. The method of claim 4, wherein a monoisocyanate is used in Stage (I) in an amount up to 2 gram-equivalents of —NCO groups per gram-equivalent of

group present in the silane, and the product obtained from Stage (I) is heated to a temperature in the range of from 110° C. to 200° C. for at least two minutes in Stage (II) after or during the addition of additional isocyanate.

6. The method of claim 4, wherein a diisocyanate is used in Stage (I) in an amount up to 3 gram-equivalents of —NCO groups per gram-equivalent of

group present in the silane and the product obtained from Stage (I) is heated to a temperature in the range of from 110° C. to 200° C. for at least two minutes in Stage (II) after or during the addition of additional isocyanate.

7. The silicon compounds obtained in claim 2, wherein the temperature in (II) is from 120° C. to 170° C.

8. The silicon compounds obtained in claim 3, wherein the temperature in (II) is from 120° C. to 170° C.

9. The method of claim 5, wherein the temperature in (II) is from 120° to 170° C.

10. The method of claim 6, wherein the temperature in (II) is from 120° to 170° C.

11. The silicon compounds obtained in claim 1, wherein the diisocyanate is an aliphatic diisocyanate.

12. The silicon compounds obtained in claim 3, wherein the diisocyanate is an aliphatic diisocyanate.

13. The method of claim 4, wherein the diisocyanate is an aliphatic diisocyanate.

14. The method of claim 6, wherein the diisocyanate is an aliphatic diisocyanate.

* * * * *